United States Patent [19]

Diem et al.

[11] 4,080,383
[45] Mar. 21, 1978

[54] PRODUCTION OF FORMALDEHYDE

[75] Inventors: Hans Diem, Mannheim; Guenther Matthias; Oskar Hussy, both of Ludwigshafen, all of Germany

[73] Assignee: Badische Anilin- & Soda-Fabrik Aktiengesellschaft, Ludwigshafen am Rhein, Germany

[21] Appl. No.: 351,156

[22] Filed: Apr. 16, 1973

[30] Foreign Application Priority Data

Apr. 27, 1972 Germany ............................ 2220665

[51] Int. Cl.² ............................................. C07C 45/16
[52] U.S. Cl. ................................................. 260/603 C
[58] Field of Search ...................... 260/603 HF, 603 C

[56] References Cited
FOREIGN PATENT DOCUMENTS 1,133,357   2/1963   Germany ..................... 260/603 HF

OTHER PUBLICATIONS

Skvortsov et al., Chemical Abstracts, vol. 51, Col. 18391, Nov. 1957.
Oratovskii, V.I., Chemical Abstracts, vol. 55, Col. 6057, 1961.

*Primary Examiner*—James O. Thomas, Jr.
*Assistant Examiner*—W. B. Lone
*Attorney, Agent, or Firm*—Keil, Thompson & Shurtleff

[57] ABSTRACT

The production of formaldehyde by oxidizing dehydrogenation of methanol in the presence of a silver catalyst using air which has been washed with a solution of an alkali metal compound in water and methanol in specific proportions. The product is a disinfectant, tanning agent, reducing agent and a starting material for the production of synthetic resins, adhesives and plastics.

7 Claims, No Drawings

PRODUCTION OF FORMALDEHYDE

The invention relates to a process for the production of formaldehyde by oxidizing dehydrogenation of methanol in the presence of a silver catalyst using air which has been washed with a solution of an alkali metal compound in water and methanol in specific proportions.

Various methods for the production of formaldehyde by oxidizing dehydrogenation of methanol with air in the presence of a silver catalyst at elevated temperature are described in Ullmanns Encyklopadie der technischen Chemie, volume 7, pages 659 et seq. The permeability of the catalyst declines in the course of time so that output decreases. In consequence the catalyst has only a limited life and eventually has to be replaced. The yield of pure end product falls while the amount of unreacted methanol increases. These two effects are also caused by inactivation of the catalyst which in severe cases is termed catalyst poisoning. An essential factor in catalyst poisoning is the effect of extraneous substances which are contained in the air used for the oxidation. Such air pollution occurs to a special extent in industrial areas where the atmosphere may contain the following catalyst poisons: hydrogen sulfide, sulfur dioxide, hydrogen chloride, hydrogen fluoride, halogens, volatile halogen compounds such as carbon tetrachloride; ammonia and amines such as monomethylamine, dimethylamine and trimethylamine; arsenic and antimony compounds such as arsenic trioxide and antimony trioxide; acetylene; phosphorus compounds such as phosphine; soot; iron oxide powder; hydrogen cyanide; carbon monoxide; extraneous substances formed by anaerobic decomposition of proteinaceous waste such as mercaptans, indole and skatole; oxides of nitrogen; lead compounds such as lead tetraethyl and lead tetramethyl; organic compounds such as 3,4-benzopyrene, fluoranthrene, pyrene and phenanthrene which pass into the atmosphere in motor car exhaust gas, and their oxidation products such as acrolein. The amount of extraneous substances present in the atmosphere is generally from 0.01 to 10 ppm.

Austrian patent specification No. 218,492 discloses a method of passing air for purification through a dust filter and then washing it with from 5 to 10% by weight aqueous caustic soda solution, methanol, potassium permanganate solution and water. The Specifiaction explains that this method of purification is troublesome, expensive and ineffective and teaches purification of air by the use of aqueous formaldehyde solution prepared in a formaldehyde plant as the wash liquid. This method of purification is unsatisfactory however on an industrial scale. Since the temperature of a 40% formaldehyde solution has to be at least 50° C to prevent formation of polymers, the solution has a considerable vapor pressure. The vapor pressure of formaldehyde solutions increases steeply with increasing formaldehyde content and in the case of a 40% by weight solution at 55° C it is 6.3 mm Hg and in the case of 50% by weight solution at 60° C it is 15.3 mm Hg. Formaldehyde is entrained into the air in accordance with this vapor pressure and this impairs an economical and simple course of the operation and decreases the yield of end product. The entrained formaldehyde is decomposed at the silver catalyst into carbon monoxide, methanol and other byproducts (J. Chem. Phys., 19, 176 et seq. (1951); Rec. Trav. Chim. Pays-Bas, 58, 39 et seq. (1939)). When the air is strongly contaminated the pollutants pass into the formaldehyde solution in an appreciable amount and this gives rise to trouble in subsequent operations. Acid pollutants are not removed satisfactorily because the formaldehyde solution itself is acid.

Ind. Eng. Chem., 44, 1514 (1952) discloses a method of washing the air for the reaction with 5% by weight aqueous caustic soda solution to remove extraneous substances. An article in Chem. Eng. (London) (1949), page 132 and Ullmanns Encyklopadie der technischen Chemie, volume 7, page 660 also describe methods of washing air with caustic soda solution or soda solution. Scrubbers having a height of from 3 to 6 meters are used. The purification effect in these methods is unsatisfactory, especially when there is a high throughput of air in industrial operation.

The object of the invention is to provide a new process for producing formaldehyde in a better space-time yield and higher purity and in some cases in a simpler and more economical manner.

This object is achieved in the oxidizing dehydrogenation of methanol with air in the presence of a silver catalyst at elevated temperature by carrying out the reaction with air which has been washed with an aqueous solution of from 4 to 20% by weight of an alkali metal compound and of 0.5 to 4% by weight of methanol.

The process of the invention surprisingly gives formaldehyde in better space-time yields and higher purity than the prior art methods and in some cases it is simpler and more economical. The efficiency of the air wash is better and consequently the life of the catalyst is prolonged. Poisoning of the catalyst by the reaction air is avoided and so is an enrichment of pollutants in the solution of the end product. Smaller scrubbers, preferably of a height of from 0.8 meter to 1.8 meters, may be used because of the good washing efficiency and operation is thus simplified and the economy of the plant is increased.

Washing is advantageously carried out with an aqueous solution of from 5 to 12% by weight of an alkali metal compound and of from 0.6 to 3% by weight of methanol, preferably in a molar ratio of alkali metal compound to methanol of from 3 : 1 to 8 : 1. The hydroxides, carbonates, salts of weak or polybasic acids, and alkoxides of the alkali metals, particularly of sodium, are advantageous alkali metal compounds. Examples are as follows: potassium hydroxide, sodium hydroxide, potassium carbonate, sodium carbonate, lithium carbonate, sodium acetate, sodium propionate, sodium ethylene glycolate, sodium methylate, sodium ethylate, and sodium tripropylene glycolate. Caustic soda solution and sodium carbonate solution are preferred because they are cheap.

Pure methanol, commercial methanol or advantageously mixtures thereof with water or condensed water are suitable starting materials for the production of formaldehyde; the concentration of the aqueous mixtures may conveniently vary within the range from 50 to 95% and preferably from 60 to 90% by weight. In an advantageous embodiment the feedstock is crude methanol which has been purified by separation of a fraction of low boiling point or by treatment with oxidizing agents and/or alkalies by methods described in German Printed Application No. 1,277,834 or German Pat. Nos. 1,235,881 and 1,136,318. The methanol is generally supplied to the reaction zone in vapor phase and may be mixed with inert gas. Nitrogen is an example of a suitable inert gas for use in the process. Pure, commercial or crude methanol may be used for scrubbing the reaction air.

Air is used as the oxidizing agent for the production of formaldehyde. Air an methanol are conveniently used in a molar ratio of air to methanol of from 1.4 : 1 to 2.9 : 1.

The reaction air is washed using a ratio of from 300 to 5000, preferably of from 1000 to 3000, parts by volume of air to each part by volume of aqueous wash solution containing alkali compound and methanol. Washing is carried out as a rule in scrubbers, the wash liquid being supplied for example to the top of the column and the reaction air being conveniently passed countercurrent from the still up through the column. Sieve plate, Oldershaw, glass plate, bubble tray, valve plate or packed columns or columns having rotating inserts may be used as scrubbing columns. It is advantageous to use a plate column which permits a velocity of from 0.03 to 0.8 part by volume of wash solution introduced per hour into the column per part by volume of the total volume of the column. In a bubble tray column the ratio of weir height to diameter of from 0.2 : 1 to 0.4 : 1 is preferred, and in ball valve plate columns and sieve plate columns orifice diameters of from 5 to 15 mm, ball diameters of from 8 to 30 mm and distances between plates of from 300 to 800 mm are preferred. Convenient feed rates are from 30 to 80 metric tons of wash solution per hour per square meter of column cross-section and a convenient throughput is from 30 to 100 metric tons of air per hour per square meter of column cross-section. Scrubbing is carried out as a rule at a temperature of from 30° to 150° C, preferably from 60° to 120° C (measured at the top of the column) at atmospheric or superatmospheric pressure, batchwise or preferably continuously.

An advantageous embodiment makes use of an alkaline crude methanol which has been purified by one of the methods mentioned above as the feedstock. Such a crude methanol generally contains from 0.10 to 0.30% by weight of alkali compound, usually sodium hydroxide. It is continuously vaporized in the evaporator column of the formaldehyde plant in the form of an aqueous mixture as described above. The bottoms of the column contains a mixture of alkali, methanol and water which generally has a composition of from 4 to 20% by weight of alkaline compound and from 0.6 to 3% by weight of methanol, with reference to water. The alkaline compounds are mainly sodium hydroxide, sodium formate and sodium carbonate. In large scale operation the bottoms of the evaporator has a volume of from 2 to 3 $m^3$ and is continuously removed. The composition may be for example: 1.0% of methanol, 5.5% of sodium hydroxide, 4.2% of sodium formate, 1.2% of sodium carbonate, 88.1% of water. Traces of copper, iron, calcium and silicon as well as organic constituents which are generally less than 2% by weight based on water are also usually present. This evaporator bottoms may be recycled in the wash column and the reaction air scrubbed countercurrent or cocurrent. The air may also be passed direct through the evaporator bottoms, washed therein and then passed through the trays of the evaporator column. The bottoms then acts like a bubble column. In spite of the foreign substances introduced with the crude methanol, this scrubbing surprisingly results in satisfactory purification of the reaction air. This embodiment also has the advantage that some of the methanol contained in the evaporator bottoms is entrained by the air so that less methanol is lost or contaminates the waste water. In a similar way mixtures of pure or technical methanol and water may be evaporated, alkali in the amount according to the invention may be added to the bottoms of the evaporator and the bottoms mixture used as wash liquid. In the evaporation of all these mixtures it is advantageous to allow such an amount of liquid to evaporate that the bottoms occupies from the sixtieth to two hundredth part of the original total volume. In such cases the evaporator column conveniently has two to four trays. If necessary the concentration of the aqueous methanol mixture is changed or its rate of evaporation is regulated so that the quantitative relationship of the components in the wash solution is maintained in the bottoms.

In other respects the process for the production of formaldehyde is carried out as usual. Any silver catalyst is suitable for the process of the invention, for example those described in German Patent Application DAS 1,231,229 and Ullmanns Encyklopadie der technischen Chemie, volume 7, pages 659 et seq. It is preferred to use a two-layer silver catalyst, for example one of the catalysts disclosed in German Patent Application DAS 1,294,360 and German patent application No. P 19 03 197.1. The said publications may be referred to for details of the production of the catalyst and of carrying out the appropriate reaction with the catalyst. A preferred embodiment of the process according to the invention consists in carrying out the reaction in contact with a two-layer catalyst, the lower layer having a thickness of from 15 to 40 mm and particularly from 20 to 30 mm and consisting at least to the extent of 50% by weight of crystals having a particle size of from 1 to 4 mm and particularly from 1 to 2.5 mm, and the upper layer having a thickness of from 0.75 to 3 mm and particularly from 1 to 2 mm and consisting of crystals having particle sizes of from 0.1 to 1 and particularly of 0.2 to 0.75, and loading this catalyst with from 1 to 3 metric tons and particularly from 1.4 to 2.4 metric tons of methanol per $m^2$ of catalyst bed cross-section per hour. In industrial operation it is preferred to use a catalyst bed diameter of at least 0.5 meter and conveniently from 1 to 3 meters. In the case of a catalyst in a single layer the preferred loading may similarly be from 1 to 3 metric tons and particularly from 1.4 to 2.4 metric tons of methanol per $m^2$ of catalyst bed cross-section per hour.

In other respects the oxidation is carried out in a conventional manner for example by passing a vapor/-gas mixture of methanol vapor, washed air, condensate vapor and optionally inert gas and additional steam in the amounts stated above at a temperature of from about 550° to 780° C and particularly from 640° to 750° C through the silver catalyst. It is advantageous for the reaction gas leaving the catalyst zone to be cooled within a short time, for example in less than 0.2 second, for example to a temperature of from 50° to 170° C. The cooled gas mixture is then conveniently fed into an absorption tower in which the formaldehyde is scrubbed from the gas mixture with water advantageously countercurrent. Some of the offgas remaining is allowed to escape and the remainder is conveniently recycled to the reaction.

The process is generally carried out at a pressure of from 0.5 to 2 atmospheres, preferably from 0.8 to 1.8 atmospheres, batchwise or preferably continuously.

The formaldehyde which can be prepared by the process of the invention is a disinfectant, tanning agent, reducing agent and a valuable starting material for the production of synthetic resins, adhesives and plastics.

Ullmann, volume 7, page 670 may be referred to for details of use.

The following Examples illustrate the invention. The parts specified are by weight. They bear the same relation to parts by volume as the kilogram to the liter. The yields given are percentages of the theoretical yield based on the weight of the starting methanol (calculated as 100%)

EXAMPLE 1

The plant used comprises a crude methanol evaporator (a column having two sieve-plates), a scrubber packed with Raschig rings and having a length of 1.5 meters, and a vertical tubular reactor. The reactor contains a catalyst in two layers of which the lower layer has a thickness of 25 mm and consists to the extent of 70% by weight of crystals having a particle size of from 1 to 2.5 mm and the upper layer has a thickness of 1.5 mm and consists of crystals having particle sizes of from 0.2 to 0.75 mm. The reactor communicates with an absorption column. A mixture of 4.6 parts of crude methanol (prepared by a high pressure method) containing 0.0083 part of sodium hydroxide, and 3.1 parts of water is supplied per hour to the evaporator and vaporized therein at 92° C and 1.3 atmospheres. During each hour a total of 0.16 part of evaporator residue is obtained and this is supplied continuously to the wash liquid to be circulated in the scrubber. 42 parts of evaporator residue per hour per square meter of the cross-section of the scrubber, consisting of 1.0% by weight of methanol, 5.8% by weight of sodium hydroxide, 3.9% by weight of sodium formate, 1.4% by weight of sodium carbonate, 0.9% by weight of organic residue and 87.0% by weight of water is continuously pumped in circulation as wash liquid over the top of the scrubber, 0.16 parts of scrubbing liquid is removed from the circulation per hour. The wash liquid is passed at 70° C and 1.4 atmospheres downwardly and reaction air is passed upwardly countercurrent at the rate of 8.3 parts per hour per square meter of column cross-section. The air washed in this way is mixed with the vaporized mixture of methanol and water from the evaporator and the vapor mixture is passed at 690° C and a total pressure of 1.15 atmospheres and a loading of 2.04 metric tons of methanol per m$^2$ of catalyst bed cross-section per hour over the bed of catalyst of finely divided silver, cooled to 150° C and dissolved in 20.1 parts of water in a packed tower. A mixture of 3.8 parts of formaldehyde (88.16% of theory), 0.014 part of methanol (= 1.1% by weight based on the whole solution) and 0.00028 part of formic acid is obtained.

The rise in pressure caused by the resistance offered by the catalyst is only 228 mm of Hg in the reaction zone even after operation for 100 days. The life of the catalyst is prolonged to 100 days from the 60 days' life when the air used is not purified. Conversion of methanol remains constant at 98.5% of theory. The yield of end product and the content of formic acid in the formaldehyde solution obtained do not change during 90 days.

EXAMPLE 2

Washing and reaction are carried out as described in Example 1 but 0.107 part per hour of a fresh solution of 0.005 part of alkali metal hydroxide and 0.002 part of methanol in 0.100 part of water is used as wash liquid instead of the evaporator bottoms. 3.8 parts (88.18% of theory) of formaldehyde, 0.00023 part of formic acid and 0.104 part of methanol (= 1.1% based on the whole solution) are obtained per hour. The yield of end product, the content of formic acid and the conversion (98.5% of theory) remain constant over 100 days. The increase in pressure is only 152 mm after 100 days. The life of the catalyst is 120 days.

When crude methanol is used in a reaction in which the reaction air is not washed, the yield is 87.5% of theory, the formic acid content is 0.00057 part, the conversion is 97.14% of theory, and increase in pressure is 304 mm after 50 days and the life of the catalyst is 60 days.

We claim:

1. A process for the production of formaldehyde by oxidizing dehydrogenation of methanol with air in the presence of a silver catalyst at elevated temperature wherein the reaction is carried out with air which has been scrubbed with an aqueous solution of 4 to 20% by weight of one or more alkali metal compounds selected from the group consisting of an alkali metal hydroxide, carbonate, alkoxide and salt of a weak or polybasic acid, said aqueous solution also containing 0.5 to 4% by weight of methanol.

2. A process as claimed in claim 1 wherein the air is washed with an aqueous solution of from 5 to 12% by weight of an alkali metal compound and of from 0.6 to 3% by weight of methanol.

3. A process as claimed in claim 1 wherein the scrubbing of the air is carried out in a ratio of from 300 to 5000 parts by volume of air per part by volume of aqueous washing solution containing said alkali metal compound or compounds and methanol.

4. A process as claimed in claim 1 wherein the air is scrubbed at a temperature of from 30° to 150° C.

5. A process as claimed in claim 1 wherein the scrubbing of the air is carried out at a temperature of from 60° to 120° C.

6. A process as claimed in claim 1 wherein the scrubbing of the air is carried out with a mixture of alkali, methanol and water having the composition: from 4 to 20% by weight of said alkali metal compound or compounds and from 0.6 to 3% by weight of methanol based on water which mixture is the bottoms in the evaporator column of the formaldehyde production plant, the air being passed direct through the evaporator bottoms.

7. A process as claimed in claim 1 wherein the methanol of said aqueous solution is crude methanol.

\* \* \* \* \*